(12) United States Patent
Goldstein

(10) Patent No.: US 8,019,553 B1
(45) Date of Patent: Sep. 13, 2011

(54) METHOD OF MODELING FOR DRUG DESIGN, EVALUATION, AND PRESCRIPTION IN THE TREATMENT OF DISEASE

(76) Inventor: Michael Goldstein, Ridgefield, CT (US)

( * ) Notice: Subject to any disclaimer, the term of this patent is extended or adjusted under 35 U.S.C. 154(b) by 510 days.

(21) Appl. No.: 10/938,394

(22) Filed: Sep. 9, 2004

(51) Int. Cl.
*G06F 7/00* (2006.01)
(52) U.S. Cl. ............... 702/19; 702/20; 703/11; 707/700
(58) Field of Classification Search .................. None
See application file for complete search history.

(56) References Cited

U.S. PATENT DOCUMENTS

2003/0104475 A1* 6/2003 Kelly et al. .................... 435/7.1
2005/0131663 A1* 6/2005 Bangs et al. .................... 703/11

OTHER PUBLICATIONS

Perelson, A. Modelling viral and immune system dynamics; 2002, Nature Reviews, vol. 2, pp. 28-36.*
Wigginson et al. A model to Predict Cell-Mediated Immune Regulatory Mechanisms During Human Infection with *Mycobacterium tuberculosis*; 2001 Journal of Immunology: 166, 1951-1967).*
Immunology for physicists, Perelson, et al., Reviews of Modern Physis, vol. 69, No. 4, Oct. 1997.

* cited by examiner

*Primary Examiner* — Mary Zeman
(74) *Attorney, Agent, or Firm* — Ladas & Parry LLP

(57) ABSTRACT

The present invention encompasses utilizing a model of disease, immune response, and dynamic (time-dependent) drug therapy. In the embodiments an optimal dynamic therapy from one or more compounds is selected for the treatment of infectious disease.

17 Claims, 3 Drawing Sheets

Figure 1: Flow chart of pathways and model variables. A partial list of Cytokines and promoting / down-regulating actions is shown.

Figure 2: Normalized evolution of bacterial (solid) and cytotoxic (dashed) populations.

Figure 3: Populations in an analog of Crohn's disease for: (1) bacteria; (2) cytotoxic & macrophage cells, and (3) phagocytic cells.

Figure 4: Modeled evolution (solid lines) and empirical evolution (dotted lines with symbols) for : (1) bacteria; (2) cytotoxic cells; and (3) phagocytic cells.

FIG. 5

| Table 1: Parameters used in the modeling of figures 2 – 4. | | | |
|---|---|---|---|
| Parameter | Fig. 2 | Fig. 3 | Fig. 4 |
| $I_o$ | 0.215 | 0.1 | 0.366 |
| $K$ | 0.5 | 0.6667 | 0.4116 |
| $\xi_Q Q$ | 0.00086 | 0.000618 | 0.035 |
| $d_1 / d_2$ | 0.25 / 0 | 0 / 0 | 0 / 0 |
| $\xi_C / \xi_P$ | 0.1164 / 0 | 0.1 / 0.1 | 1.5 / 1.5 |
| $\varepsilon_I / \varepsilon_C / \varepsilon_P$ | 0.1 / 2.5 / 0 | 0.01 / 0.01 / 0.01 | 0.001 / 0.6 / 0.01 |
| $C_f / P_f$ | 0.01 / 0 | 1.617 / 0.808 | 0.02683 / 0.00618 |
| $\tau_C / \tau_P$ | 0.25 / 0 | 0.25 / 0.25 | 1.4433 / 0.01 |
| $C_O / P_O$ | 0.85 / 0 | 0.6 / 0.6 | 2.08686 / 0.06 |
| $C_I / P_I$ | 0 / 0 | 0.75 / 0.5 | 0 / 0 |
| $\sigma_{ij} / \gamma_C / \gamma_P$ | 0 / 0 / 0 | 0 / 0 / 0 | 0 / 0 / 0 |

METHOD OF MODELING FOR DRUG DESIGN, EVALUATION, AND PRESCRIPTION IN THE TREATMENT OF DISEASE

CROSS-REFERENCE TO RELATED APPLICATIONS

The present invention is related to and claims priority under 35 U.S.C §119(e) to U.S. Provisional Patent Application Ser. No. 60/501,696, filed Sep. 9, 2003, entitled "A method of modeling for drug design, evaluation and prescription in the treatment of disease."

BACKGROUND OF THE INVENTION

The present invention relates generally to a method of understanding disease through modeling utilized to optimize drug design, evaluation, and application in medical treatment. In particular, the invention is on the utilization of a model that comprises an expression of disease, immune response, and dynamic (time dependent) drug treatment.

FIELD OF THE INVENTION

Computational immunology has developed rapidly in recent years as a sub-field of systems biology, which is an area of science that seeks to understand the functional behavior of organisms, organs, and systems through detailed modeling of its components. An advantage of these highly detailed models is a theoretical potential to obtain a precise match or calibration of computational results with experimental measurement. In practice however, the large parameter set of these models imposes two obstacles. First, it is very difficult to obtain the necessary calibration data for a large structurally identifiable parameter set. This is expected to remain an obstacle even in the foreseeable future despite the rapid advances being made in tools used for cellular, genomic, and proteomic measurement. Second, these highly complex models are often degenerate—multiple parameter sets can produce indistinguishable results for the metrics of interest. This over parameterization is a natural consequence of a highly complex and flexible immune response with redundant properties. Considerable attention has been given to these challenges with efforts to develop laboratory techniques that aid in calibration of disease/immune models. This emphasis of research on complex models of disease has resulted in a neglect of further expanding development to include the dynamic effect of medication. When drug effects have been incorporated in disease models a main interest has been in establishing the best treatment from a set of predefined constant-treatment options. Since a number of pathways play a role in the immune response to disease, the benefit of drug to a patient can depend on the relative importance of the treatment's particular biologic target in the individual's condition. For that reason, pharmacogenetic modeling to compare different treatment and individual responses has been of growing interest.

In the current invention, we use a lumped parameter model that describes an innate and/or an adaptive immune response to disease where importantly we have further included effects from dynamic drug treatment. The model's network topology follows from the underlying biology, however, where possible signaling pathways can be combined to form a logical equivalent circuit or a lumped parameter model. It is even possible that signaling pathways might be excluded from the model (either intentionally or due to lack of knowledge) with subsequent effects compensated for by other fitting parameters. The model parameters can be directly measured, obtained through regression or fitting techniques, or by a combination of the two. The present approach trades theoretically achievable precision for easier calibration and potentially greater realizable accuracy. The calibration data might come from an individual patient, however, is more likely to be derived in vivo from a group of patients using in vitro supporting data to develop a canonical calibrating data set. Drug treatment is included in the model where parameters are shown as either implicitly or explicitly time dependent. The added complexity of including dynamic drug effects (parameters that can change in time) does not necessitate use of a lumped immune parameter model however doing so offsets some of the increase in computational requirements in immunodynamic simulation.

BRIEF SUMMARY OF THE INVENTION

An immunodynamic model enables simulation of infection, immune response, and drug effects. It is the applications of such modeling and findings from its uses that are patented here.

The drug discovery and approval process typically follows from several stages. In a first stage, one or more drug targets are selected which are (biochemically) assumed to be useful for disease treatment. Many drug candidates are evaluated for effectiveness against this target in laboratory and animal experiments. However, limited dynamic modeling is conducted to aid in the design of these drug candidates or in ranking their usefulness. In a first embodiment of this invention a method of modeling is used for finding desired drug properties and ranking candidate drugs.

In a second stage of development, a chosen drug is entered into three phased trials to show efficacy and to obtain regulatory approval. This is a time consuming and expensive process. In the second embodiment of the invention, trials are made more successful by strengthening trial design. This may be done by optimizing dosing schedules to increase the desired signal to control ratio.

In clinical practice, drug prescription (selection and protocol) is dependant on the severity and stage of a disease. For the third embodiment, any device (computer, table, other) that performs or supports calculations of immunodynamic modeling such as for disease staging or optimizing treatment efficacy is claimed.

BRIEF DESCRIPTION OF THE SEVERAL VIEWS OF THE DRAWINGS

FIG. 5 is a table of the parameters used in the modeling of FIGS. 2-4.

DETAILED DESCRIPTION OF THE INVENTION

Introduction

Figure 1:
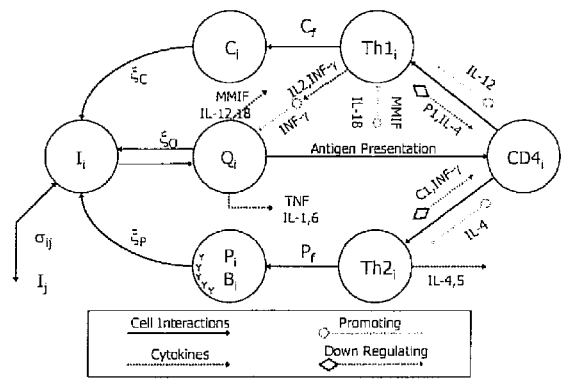
FIG. 1 is a flow chart of cellular pathways and model variables.

A generalized model of the interaction between infection, immune response, and treatment in infectious disease is hypothesized. Although this model is derived pedagogically, its utility towards understanding causation, both acute and chronic response, and the relative benefit in treatment protocols for hypothetical conditions is suggestive of a possible reason for clinical efforts to similarly model real disease.

The time dependent concentration of a medication is generally determined empirically. Nonetheless, pharmacokinetic analysis provides an analytic fit that lends intuition to practitioners. For example, utility exists in understanding the half-life of a medication. When a treatment protocol with optimal therapeutic benefit needs to be determined, however, only phenomenological dosing studies are available and analogous quantitative methods are not as well developed. Thus, a model of the interaction between infection, immune response, and treatment may be supportive with medications where clinical experience is the only guide to dosing schedules.

Many diseases correlate with both genetic factors and environmental or pathogenic stimuli. This creates indistinctness, complicating the study of causation in some conditions. The infectious and immunogenic interactions that lead to causation for both acute and chronic responses in hypothetical conditions will be analyzed.

A generalized immunodynamic model is shown here. An analog of a bacterial infection with antibiotic treatment will be modeled as an example of an acute infection and dosing schedules will be compared. An analog of Crohn's disease will be modeled and a mechanism that leads to chronic disease is shown. In order to benchmark the model, a comparison is made to a published description of influenzavirus infection.

To first order, the unimpeded rate of change for an infection, l(t), expressed as its derivative or infection velocity, dI/dt, will for pathogenic disease (pathogens, such as viruses, bacteria, protozoa, and fungi—are assumed capable of reproduction) be proportional to its state, $\sim k^*I(t)t$. However, a pathogen may also change the suitability of its environment for growth, the susceptibility of the patient to further infection, or lead to intercellular mutations that affect cellular growth and death rates. Additionally, infection from environmental factors does not exhibit growth, but is instead a function of exposure. Thus, a generalized unimpeded growth function, $f(l,t)$, can be employed. Coupling between components of the disease is also needed for inhomogeneous conditions. This is relevant, for example, when a pathogen, at least in part, evades the immune system or otherwise forms a reservoir.

Two simplified models for cell populations are used to describe the primary immune responses. The first, for example, may represent type 1 helper T (Th1) activated strong response cells. This population is intended to embody both cytotoxic cell responses and the effects from associated antiviral and macrophage-activating cytokines, such as interferon-γ (INF-γ) and tumor-necrosis-factor-α (TNF-α). The second population may for example represent type 2 helper T (Th2) mediated responses. This population is characterized by antibody-producing transformed B cells and specific phagocyte cell responses. Two additional terms are added to these population models. The first is a coupling factor to support conditions in which an immunoregulatory loop is prevalent. The differentiation from CD4 T cells to Th1 and Th2 phenotypes can for example be regulated by INF-γ from Th1 cells that inhibit Th2 production and interleukin-4 (IL-4) from Th2 cells that inhibit Th1 production. The second term added to both population models is an impeding force to embody the effect of immunodeficiency. Although cellular activation and growth rates are modeled as piecewise linear-dependent on the infection, the detailed connection to immunogenic stimuli (type 3 T cells) and cytokines should be further explored. Medications will be modeled as selectively toxic to a target or synthesis-limiting with high biochemical availability, $d_1(t)$, or with low availability, $d_2(t)$ (a medication with high availability will affect a constant fraction of a pathogens total population and a medication with a low availability will affect a time-dependent smaller fraction of the pathogens).

The infection velocity can then be expressed as $$\frac{\partial I_i}{\partial t} = \left[ [f(I_i, t) - [\xi_C C_i(t) + \xi_P P_i(t) + d_1(t)]I + \sum_j \sigma_{ij}(I_j - I_i) - [\xi_Q Q_i(t) + d_2(t)] \right] \times \begin{cases} 1, & I(t) \geq \varepsilon_1 \\ 0, & \text{Otherwise} \end{cases} \quad (1)$$

where $f(l,t)$ is the unimpeded growth rate of infection $l_i$, $\sigma_{ij}$ is the rate of diffusion from the $j^{th}$ to the $i^{th}$ component of the infection, $C_i(t)$ is the Th1 related responses (i.e., where $f(l,t)$ is the unimpeded growth rate of infection $l_i$, $\sigma_{ij}$ is the rate of diffusion from the $j^{th}$ to the $i^{th}$ component of the infection, $C_i(t)$ is the Th1 related responses (i.e., cytotoxic or other), $\xi_c$ is its fractional efficiency per unit time, $P_i(t)$ is the Th2 related responses (i.e., specific phagocytic cell population or other), $\xi_p$ is its fractional efficiency per unit time, $Q_i(t)$ is a nonspecific macrophage response, and $\xi_Q$ is its fractional efficiency per unit time.

It would be difficult to completely model the cascade of responses to infection and any attempt would likely result in over parameterization. Thus, expressions for cytotoxic and phagocytic populations should be understood as lumped variables that represent generalized effects. The immunodynamics are modeled with coupled equations.

The cytotoxic and associated antiviral and macrophage cell population is expressed by $$\frac{\partial C}{\partial t} = C(t) \times \begin{cases} (C_O - P_1 P(t)), & \geq 0 \\ 0, & \text{Otherwise} \end{cases} \times \begin{cases} 1, & I(t) \geq \varepsilon_C \\ I(t)/\varepsilon_C, & \text{Otherwise} \end{cases} + C_f I(t) - \gamma_C(I, t) - \tau_C C(t) \quad (2)$$

where the i subscript for inhomogeneous populations has been dropped for notational simplicity. This has a basic exponential growth rate of $C_O$-$\tau_c$ when an infection is present above a threshold of $\varepsilon_C$ and a decay rate of $\tau_c$ in the absence of infection with a linear dependence in between. The extrinsic term containing $P_1 P$ provides coupling to the specific phagocytic population P with an added constraint that it cannot impede growth to become negative. The term $C_f l$ is a linear rate for first-generation cell production (i.e., as from IL-12 differentiation for Th1 cells). The factor $\gamma_C(l,t)$ is an immunodeficiency function. Similarly the specific phagocytic population is expressed by $$\frac{\partial P}{\partial t} = P(t) \times \left\{ \begin{array}{l} (P_O - C_1 C(t)), \geq 0 \\ 0, \text{Otherwise} \end{array} \right\} \times \left\{ \begin{array}{l} 1, I(t) \geq \varepsilon_P \text{ or } t < t_O \\ I(t)/\varepsilon_P, \text{Otherwise} \end{array} \right\} + \quad (3)$$

$$P_f I(t) - \gamma_P(I, t) - \tau_P P(t)$$

and again the i subscript was dropped for notational simplicity. This has a basic exponential growth rate of $P_O \tau_p$ when an infection above a threshold $\varepsilon_p$ is present and a decay rate of $\tau_p$ in the absence of infection with a linear dependence in between. The factor $C_1 C$ provides coupling to the cytotoxic population C, the term $P_f I$ is a linear rate for first generation cell production (as in IL-4 differentiation for Th2 cells), and the factor $\gamma_p(l,t)$ is an immunodeficiency function.

The nonspecific immune response, Q(t), can but does not have to be modeled as a simple constant (a zero order approximation). The initial conditions for the models are chosen to describe the state just after infection. Thus, $l(t=0)=l_o$, $C(t=0)=P(t=0)=0$ can be used for a first infection and $P(t=0)=P_{IC}$ could be used if immunity exists (i.e. when memory T and B cells are present).

Although equations 1-3 are a relatively simplistic model of infection, the immune response, and drug treatment (as diagrammed in FIG. 1), it will be seen that these equations exhibit desirable properties. Although only a few populations, signaling pathways and one drug target have been included here, an expert in the field will recognize that others may be used in generalized equations that represent different network topologies.

Acute Infection

Figure 2:
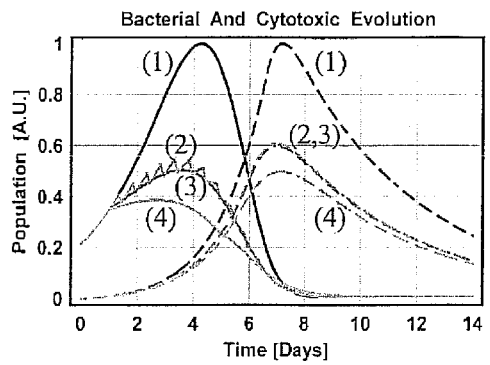
FIG. 2 is a graph of the normalized evolution of bacterial and cytotoxic populations where case (1) shows the un-medicated model. Otherwise, the same total dose of medication $d_1$ is given over days 2-9 inclusive. These had a dosing schedule of: (2) a twice daily constant oral dose; (3) a continuous baseline IV rate; and (4) a continuous IV with 50% above and below baseline rate over four days each.

An acute non-lethal infection reaches a maximum state of virulence after which the fundamental agent is overcome by the immune system. As an example of this, an analog of a bacterial infection is modeled here. A single population of immune response cells will be assumed and the efficacy of several antibiotic dosing schedules will be compared. The immunodynamic model (equations 1-3) have been solved numerically using the parameters shown in the table of FIG. 5. The results are graphed in FIG. 2 using four treatment protocols.

Of the four treatment protocols explored; (1) is the unmedicated case; (2) represents constant twice daily oral dosing; (3) is a constant IV baseline rate of medication; and (4) is a continuous IV at a rate 50% above the baseline for half the period and 50% below the baseline in the remaining half. The total amount of medication delivered (integrated dose) is the same for each case and it is given for eight days starting at the end of the first day.

The medication delivered twice daily with a constant oral dose (case 2) closely approximated the results achieved from a continuous level of medication (case 3). Here the peak of infection was reduced by ~50% and it was reached 0.7 days earlier than the un-medicated condition. It is interesting to note that a two-level protocol (case 4) achieved the best results. The peak is ~60% reduced from the un-medicated maximum and it occurs 1.6 days earlier than the un-medicated condition.

Although higher initial dosing may not always be well tolerated, these results suggest an intuitively reasonable guideline for the use of antibiotics with acute homogeneous infection. That is, for the same total dose the seriousness of an infection is reduced if higher concentrations are employed before the peak of an infection is reached so long as the minimum concentration used after the peak is sufficient to always maintain a negative infection velocity.

Chronic Condition of IBD

The pathogenic, allergenic, and immunogenic stimulus that leads to the conditions of inflammatory bowel disease (IBD) are an area of ongoing research. However, a simplified expression of the present theory for Crohn's disease and ulcerative colitis can be modeled. The former is believed to be from type 1 helper T cell (Th1) dominated responses and the latter from type 2 helper T cell (Th2) dominated responses, possibly to bacteria infiltrating the epithelial barrier. A simplified analogy of Crohn's disease will be modeled here based on a reported mechanism for possible causation. As a first step, the goal of modeling here is to check consistency of the described mechanism with chronic activity.

An excessive, self-stimulating, imbalanced immune response to infection is modeled. The immune obligates are Q antigen-presenting, nonspecific macrophage precursors to CD4 T cells predominantly differentiated into a TH1 phenotype. The Th1 cells produce INF-γ that is a macrophage-activating cytokine and also a Th2 down regulating factor (thus $C_f > P_f$). These are self-promoting reactions. The stimulated macrophage cells have also been reported to produce the pro-inflammatory cytokines TNF-α, IL-1, and IL-6.

Figure 3:
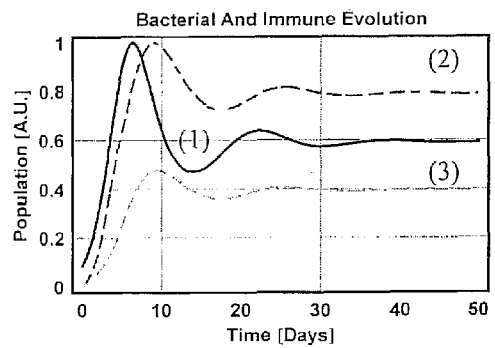
FIG. 3 is a graph of populations in an analog of Crohn's disease for (1) bacteria, (2) cytotoxic and macrophage cells, and (3) phagocytic cells.

The immune feedback loop and regulatory factors are found to be sufficient in of themselves to explain chronic behavior for the disease. Nonetheless, a mechanism to initiate the reaction and localize skip lesions in the presence of diffusion is needed. Thus, the model will include an initial source of infection ($l_o>0$). Furthermore, it was found that it must satisfy the inequality $l_o > \xi_Q Q/k$ to be capable of triggering more than a decaying (acute) reaction. The pathogenesis assumed is a small infiltration of bacteria into the mucosal immune tissue, possibly aided by ingested antigens. Although inflammation could increase susceptibility to further infection, this was not included in the model. Thus, only moderate disease activity is simulated here with a goal towards understanding why the chronic (equilibrium) should exist. The system was modeled using the parameters in the table of FIG. 5 and the results are shown in FIG. 3.

The following observations are made. First, a minimum initial infection is needed, otherwise the pathogen is overcome and the chronic does not occur. Second, the self-promoting reactions can be responsible for the imbalanced immune response even at equilibrium. Last, the down regulatory factors not only limit the excessive immune response, they enable a stable solution. It is interesting to find that in some individuals a pathogen can promote chronic infection without resorting to evasion or subversion of the immune system.

Benchmarking

Figure 4:
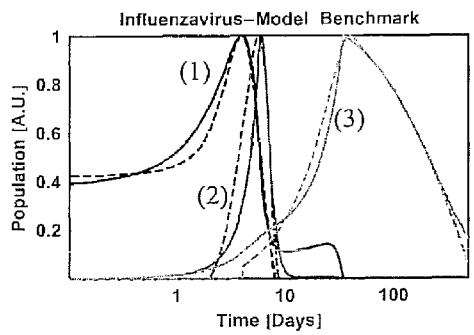
FIG. 4 is a graph showing modeled evolution and empirical evolution for (1) bacteria, (2) cytotoxic cells, and (3) phagocytic cells.

The immunodynamic model of equations 1-3 seems reasonable. However, physical relevance can not be assumed thus far and considerable verification is of course needed. This process is started here by benchmarking the model against a canonical description of intranasal influenzavirus infection. Data was taken from published graphs and interpolated with cubic splines. Regression was employed to determine model parameters. The reported data and model fit are shown together in FIG. 4 with parameters located in the table of FIG. 5. Although global optimization could improve the fit, generally good agreement was found. A discrepancy is that viral counts fall below detectable levels at the tail-end of the infection and the model requires some level of antigens present during periods of increasing immunity. A component of this may be expected from reactions following antigen-presentation and major histocompatibility complex restriction. The model comprehends this by separating first cell generation from present population growth. The discrepancy a the low pathogen levels connected to quenching growth could be removed by including a model for type 3 T cells as noted earlier although this added complexity may not be warranted.

CONCLUSION

A generalized model of immunodynamics has been derived. The approach is based on coupled differential equations for pathogen and immune cell populations and reported interactions in pathenogenisis and immunology. The usefulness of this as a strategy was motivated by modeling an acute infection with different treatment and examining the possible causation of a chronic condition. Other applications of this approach are envisioned.

Although the foregoing description has been given by way of a preferred embodiment, it will be understood by those skilled in the art that other forms of the invention falling within the ambit of the following claims are contemplated.

What is claimed is:

1. A method implemented on a specifically programmed computer having at least one processor and at least one memory coupled to said at least one processor to optimize the efficacy of a drug therapy used in the treatment of disease, said method comprising:
   a. generating a parametrized mathematical model of immune response to disease;
   b. modeling one or more drug targets with time-dependent variables that can change during the drug therapy;
   c. determining the responses of the model to a series of drug therapies; and
   d. selecting a therapy based on the determined responses of the model;
   wherein steps a to c are performed using said at least one processor.

2. The method of claim 1, wherein the disease is an infection that is pathogenic, the drug targets the pathogen or its replication process, and the method further comprises optimizing the treatment efficacy by adjusting the time dependent dose given during the therapy.

3. The method of claim 2, wherein the pathogen is bacteria, the drug is antibiotic, and the method further comprises utilizing a drug dose in a first part of the therapy that is higher than the dose used in a second part of the therapy.

4. The method of claim 1, wherein the disease is an infection that triggers an inflammatory process, the drug targets an immune signaling pathway including a cytokine, chemokine, hormone or immunoglobulin, and the method further comprises optimizing the treatment efficacy by adjusting the time dependent dose given during the therapy.

5. The method of claim 1, wherein the drug is a chemical compound or a biologic compound such as monoclonal, polyclonal, or antibody.

6. A method implemented on a specifically programmed computer having at least one processor and at least one memory coupled to said at least one processor to optimize the efficacy of a drug therapy used in the treatment of disease, said method comprising:
   a. generating a parametrized mathematical model of immune response to disease;
   b. modeling one or more drug targets with time-dependent variables that can change during the drug therapy;
   c. determining the responses of the model to a series of drug therapies encompassing compounds with different degrees of specificity of interaction with and effectiveness on the targets;
   d. simulating efficacy and optimizing the therapy for each compound; and
   e. selecting one or more compounds and its associated optimal therapy based on results obtained in step d;
   wherein steps a to d are performed using said at least one processor.

7. The method of claim 6, wherein the disease is an infection that is pathogenic, the drug targets the pathogen or its replication process, and the method further comprises optimizing the treatment efficacy by adjusting the time dependent dose given during the therapy.

8. The method of claim 7, wherein the pathogen is bacteria, the drug is antibiotic, and the method further comprises utilizing a drug dose in a first part of the therapy that is higher than the dose used in a second part of the therapy.

9. The method of claim 6, wherein the disease is an infection that triggers an inflammatory process, the drug targets an immune signaling pathway including a cytokine, chemokine, hormone or immunoglobulin, and the method further comprises optimizing the treatment efficacy by adjusting the time dependent dose given during the therapy.

10. The method of claim 6, wherein the drug is a chemical compound or a biologic compound such as monoclonal, polyclonal, or antibody.

11. A method implemented on a specifically programmed computer having a processor and a memory coupled to said processor to optimize the efficacy of a drug therapy used in the treatment of disease, said method comprising:
    a. generating a lumped-parameter mathematical model of immune response to infection;
    b. including in the model time dependent variables that represent one or more drug targets;
    c. determining the responses of the model to a series of drug therapies comprising compounds with different degrees of specificity of interaction with and effectiveness on the targets;
    d. simulating efficacy and optimizing the therapy for each compound; and
    e. selecting a compound and its associated optimal therapy based on results obtained in step d;
    wherein steps a-d are performed using said processor.

12. The method of claim 11, wherein the infection is pathogenic, the drug targets the pathogen or its replication process, and the method further comprises optimizing the treatment efficacy by adjusting the time dependent dose given during the therapy.

13. The method of claim 12, wherein the pathogen is bacteria, the drug is antibiotic, and the method further comprises utilizing a drug dose in a first part of the therapy that is higher than the dose used in a second part of the therapy.

14. The method of claim 11, wherein the infection is an inflammatory process, the drug targets an immune signaling pathway including a cytokine, chemokine, hormone or immunoglobulin, and the method further comprises optimizing the treatment efficacy by adjusting the time dependent dose given during the therapy.

15. The method of claim 11, wherein the drug is a chemical compound or a biologic compound such as monoclonal, polyclonal, or immunoglobulin antibody.

16. A method to optimize the efficacy of a drug therapy used in the treatment of disease that comprises:
    a. generating a parametrized mathematical model of immune response to disease;
    b. modeling one or more drug targets with time-dependent variables that can change during the drug therapy;
    c. determining the responses of the model to a series of drug therapies;

d. selecting a therapy based on the determined responses of the model; and e. administering the selected therapy to a subject.

17. The method of claim 16, wherein the disease is an infection that is pathogenic, the drug targets the pathogen or its replication process, and the method further comprises optimizing the treatment efficacy by adjusting the time dependent dose given during the therapy.

* * * * *